(12) United States Patent
Mukerjee et al.

(10) Patent No.: US 6,225,488 B1
(45) Date of Patent: May 1, 2001

(54) RUTHENIUM OR OSMIUM CATALYSTS FOR OLEFIN METATHESIS REACTIONS

(75) Inventors: Shakti L. Mukerjee, Louisville, KY (US); Vernon L. Kyllingstad, Floyds Knobs, IN (US)

(73) Assignee: Nippon Zeon Co., Ltd., Tokyo (JP)

( * ) Notice: Subject to any disclaimer, the term of this patent is extended or adjusted under 35 U.S.C. 154(b) by 0 days.

(21) Appl. No.: 09/285,250

(22) Filed: Apr. 2, 1999

(51) Int. Cl.[7] .............................. C07F 15/00; B01J 31/00
(52) U.S. Cl. ......................... 556/22; 556/23; 556/28; 556/136; 556/137; 502/155
(58) Field of Search .................. 556/22, 23, 28, 556/136, 137; 502/155

(56) References Cited

U.S. PATENT DOCUMENTS

| | | | |
|---|---|---|---|
| 4,883,851 | 11/1989 | Grubbs et al. | 526/268 |
| 5,198,511 | 3/1993 | Brown-Wensley et al. | 526/113 |
| 5,312,940 | 5/1994 | Grubbs et al. | 556/136 |
| 5,468,819 | 11/1995 | Goodall et al. | 526/171 |
| 5,554,778 | 9/1996 | Beatty et al. | 556/21 |
| 5,559,262 | 9/1996 | Beatty et al. | 556/20 |
| 5,569,730 | 10/1996 | Goodall et al. | 526/282 |
| 5,599,962 | 2/1997 | Beatty et al. | 556/21 |
| 5,677,405 | 10/1997 | Goodall et al. | 526/281 |
| 5,689,003 | 11/1997 | Beatty et al. | 564/278 |
| 5,710,298 | 1/1998 | Grubbs et al. | 556/22 |
| 5,728,785 | 3/1998 | Grubbs et al. | 526/142 |
| 5,728,917 | 3/1998 | Grubbs et al. | 585/653 |
| 5,750,815 | 5/1998 | Grubbs et al. | 585/511 |
| 5,811,515 | 9/1998 | Grubbs et al. | 530/330 |
| 5,831,108 | 11/1998 | Grubbs et al. | 556/21 |

FOREIGN PATENT DOCUMENTS

WO 98/21214   5/1998   (WO).

OTHER PUBLICATIONS

Abstract of EP 839,821–A2 (May 6, 1998).
Cox, et al., J. Chem. Soc. Dalton Trans., 1991, pp 2013–2018.
Fu, et al., J. Am. Chem. Soc., 1993, 115, pp 9856–9857.
Herrmann, et al., Angew. Chem. Int. Ed Engl., 1996, 35 No. 10, pp 1087–1088.
Schrock, et al., J. Am. Chem. Soc., 1990, 112, pp 3875–3886.
Nguyen, et al., J. Am. Chem. Soc., 1992, 114, pp 3974–3975.
Cox, et al., Inorg. Chem., 1990, 29, pp 1360–1365.
Cox, et al., J. Chem. Soc., Chem. Commun., 1988, pp 951–953.
Porri, et al., Tetrahedron Letters No. 47, 1965, pp.4187–4189.

*Primary Examiner*—Porfirio Nazario-Gonzalez
(74) *Attorney, Agent, or Firm*—Armstrong, Westerman, Hattori, McLeland & Naughton, LLP

(57) ABSTRACT

Penta-coordinated ruthenium or osmium catalysts for metathesis reactions of olefins, which are cationic complexes represented by formulas I, II or III:

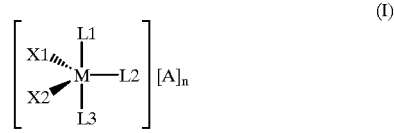

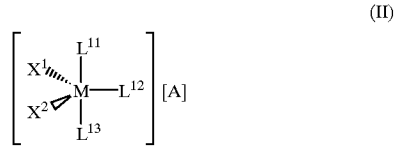

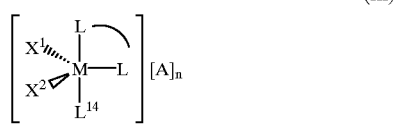

wherein M is ruthenium or osmium; each of $X^1$ and $X^2$, which may be the same or different, is an optionally substituted $C_3$–$C_{20}$ hydrocarbon group having an allyl moiety as an end group bonded to the central metal atom M, or $X^1$ and $X^2$ together form a group, optionally substituted, which results from dimerization of an alkene and has at each end an allyl moiety bonded to the central metal atom M, $L^1$ is a neutral electron donor ligand; $L^2$ is a carbene group; $L^3$ is a neutral electron donor ligand which may be the same as or different from $L^1$, or $L^3$ is a halide group; $L^{11}$ is a neutral electron donor ligand; $L^{12}$ is a solvent molecule capable of coordination to the central metal atom M; $L^{13}$ is an alkyl group; $L^{14}$ is an alkyl, a carbene, a solvent molecule capable of coordination to the central metal atom M, or a halide; L⌒L is a bidentate ligand coordinated to the central metal atom M through two atoms which may be the same or different, each of which is independently selected from the group consisting of a phosphorus atom, a nitrogen atom and an arsenic atom; A is a counter anion coordinated to the central metal atom M but only weakly coordinated so that A is not bonded as a ligand to the central metal atom M; and n is 1 or 2.

20 Claims, No Drawings

RUTHENIUM OR OSMIUM CATALYSTS FOR OLEFIN METATHESIS REACTIONS

BACKGROUND OF THE INVENTION

The present invention relates to highly active catalysts for olefin metathesis reactions, and the preparation of the catalysts. The invention also relates to the olefin metathesis reactions catalyzed with the catalysts of the invention.

A number of catalysts have been developed recently for initiating olefin metathesis reactions, including ring-opening metathesis polymerization (ROMP) of cyclo-olefins, ring-closing metathesis (RCM) of dienes to form ring-closed products, depolymerization of unsaturated polymers to form the depolymerized products, synthesis of telechelic polymers by reaction of a cyclic olefin with a functionalized olefin, and synthesis of cyclic olefins by self-metathesis of an acyclic olefin or cross-metathesis of two acyclic olefins. Those well defined catalysts usually have a metal-carbon double bond (metal-carbene or -alkylidene) that can coordinate to the alkene moiety of the olefin and, for example, can initiate readily the ring opening of cyclo-olefin monomers. Most of the metals that exhibit remarkable activity in such catalysts are second-or third-row mid-to late- transition metals. Although the specific reason for their degree of activity has not been clearly established, many theories have been put forward, the most prevalent of which expounds that late transition metals exhibit greater robustness towards the impurities that may inherently be present within a reaction system and consequently resist degradation.

Among olefins, cyclic olefins like norbornene (NB) or endo-dicyclopentadiene (DCPD) which possess a strained double bond can readily undergo ring opening metathesis polymerization (ROMP) because the ring opened product is thermodynamically favored. The above-mentioned catalysts are particularly active in catalyzing the ROMP of such ring-strained cyclo-olefins.

The catalysts that have received the greatest exposure in the literature by far are those designed by Schrock et al., as reported in Schrock et al., J. Am. Chem. Soc., 1990, 112, 3875, and by Grubbs's group, as reported in Nguyen et al., J. Am. Chem. Soc., 1993, 115, 9858; Nguyen et al., J. Am. Chem. Soc., 1992, 114, 3974; and Grubbs et al., WO98/21214 (1998). The Grubbs catalyst (a ruthenium carbene) is slightly more versatile than the Schrock catalyst (a molybdenum alkylidene) because of its ease of synthesis as well as its utility from a commercial viewpoint. Recently, Cox and co-workers reported in Cox et al., Inorg. Chem., 1990, 29, 1360; Cox, et al., J. Chem. Soc., Chem. Commun., 1988, 951–953; and Porri et al, Tetrahedron Letters, No. 47., 1965, 4187–4189, the synthesis of a class of metal catalysts based on ruthenium metal. These catalysts consist primarily of a bis-allyl ligand wrapping the metal, along with two or three acetonitrile ligands. Additionally, these catalysts possess a mono- or di-anion that is virtually (i.e., almost) coordinated to the metal center, which is therefore considered to be formally in the +4 oxidation state. These complexes in conjunction with a diazo ethyl acetate have been used by Herrmann's group, as reported in Herrmann et al., Angew. Chem. Int'l. Ed. Engl., 1996, 35, 1087, to investigate the polymerization (specifically the ROMP) of NB. Herrmann has conjectured that the active species in the catalyst system is a metal carbene generated in situ when the ruthenium reacts with the diazo alkyl compound (such as diazo ethyl acetate).

A disadvantage of the above catalysts is that for the ROMP of cyclic olefins these catalysts must be used with a co-catalyst such as a diazo alkyl compound, which requires special caution in handling because of the instability of the diazo group.

SUMMARY OF THE INVENTION

One aspect of the invention is to provide catalysts which are highly active in initiating metathesis reactions in olefins.

Another aspect of the invention is to provide catalysts which are highly active in the ring-opening polymerization (ROMP) of cyclo-olefin monomers without requiring the presence of a co-catalyst such as a diazo alkyl compound.

Another aspect of the invention is to provide methods for the preparation in good yield of the catalysts for metathesis reactions in olefins.

Yet another aspect of the invention is to provide a highly effective method for polymerizing olefins, in particular cyclo-olefins, using the catalysts of the invention.

DESCRIPTION OF THE INVENTION

The catalysts of the present invention are cationic complexes represented by formulas (I), (II) and (III) below, wherein the central metal atom M, which may be ruthenium or osmium, is in the +4 oxidation state, has an electron count of 14, and is penta-coordinated, and the counter-anion A is virtually coordinated to the central metal atom M. That is, the anion A is almost coordinated to the central metal atom M without being bonded as a ligand thereto.

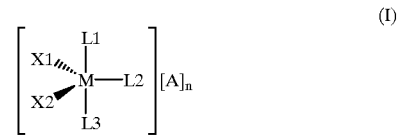

wherein M is ruthenium or osmium;

each of $X^1$ and $X^2$, which may be the same or different, is a $C_3$–$C_{20}$ hydrocarbon group having an allyl moiety as an end group bonded to the central metal atom M, said hydrocarbon group being optionally substituted on its backbone with up to three substituents independently selected from the group consisting of a $C_1$–$C_{20}$ alkyl, a $C_1$–$C_{20}$ alkoxy, and a $C_6$–$C_{20}$ aryl, and further optionally having up to three functional groups independently selected from the group consisting of hydroxyl; nitro, a halogen, thiol, thioether, ketone, aldehyde, ester, ether, amine, imine, amide, carboxylic acid, disulfide, carbonate, isocyanate, carbodiimide, carboalkoxy, and carbamate; or $X^1$ and $X^2$ together constitute a group which results from dimerization of a $C_4$–$C_{10}$ alkene and has at each end an allyl moiety bonded to the central metal atom M, said group resulting from the alkene dimerization being optionally substituted on its backbone with up to three substituents independently selected from the group consisting of a $C_1$–$C_{20}$ alkyl, a $C_1$–$C_{20}$ alkoxy, and a $C_6$–$C_{20}$ aryl, and further optionally having up to three functional groups independently selected from the group consisting of hydroxyl, nitro, a halogen, thiol, thioether, ketone, aldehyde, ester, ether, amine, imine, amide, carboxylic acid, disulfide, carbonate, isocyanate, carbodiimide, carboalkoxy, and carbamate;

$L^1$ is a neutral electron donor ligand;

$L^2$ is a carbene group represented by the formula

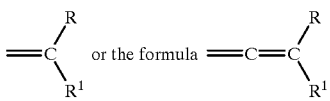

wherein each of R and $R^1$ is independently selected from the group consisting of hydrogen, $C_1$–$C_{20}$ alkyl, $C_2$–$C_{20}$ alkenyl, $C_2$–$C_{20}$ alkynyl, $C_6$–$C_{20}$ aryl, $C_1$–$C_{20}$ carboxylate, $C_1$–$C_{20}$ alkoxy, $C_2$–$C_{20}$ alkenyloxy, $C_2$–$C_{20}$ alkynyloxy, $C_6$–$C_{20}$ aryloxy, $C_2$–$C_{220}$ alkoxycarbonyl, $C_1$–$C_{20}$ alkylthio, $C_1$–$C_{20}$ alkylsulfonyl, and $C_1$–$C_{20}$ alkyl sulfinyl, wherein each of R and $R^1$ optionally may have up to three substituents selected from the group consisting of $C_1$–$C_5$ alkyl, a halogen, $C_1$–$C_5$ alkoxy, and $C_6$–$C_{10}$ aryl;

$L^3$ is a neutral electron donor ligand which may be the same as or different from $L^1$, or $L^3$ is a halide group;

A is a counter anion coordinated to the central metal atom M but only weakly coordinated so that A is not bonded as a ligand to the central metal atom M; and n is 1 when $L^3$ is a halide, and n is 2 when $L^3$ is a neutral electron donor ligand;

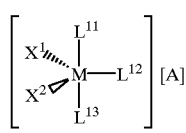 (II)

wherein M, $X^1$, $X^2$ and A are as defined above in formula (I);
$L^{11}$ is a neutral electron donor ligand;
$L^{12}$ is a solvent molecule capable of coordination to the central metal atom M; and
$L^{13}$ is a $C_1$–$C_{20}$ alkyl;

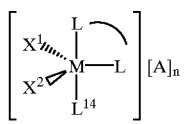 (III)

wherein M, $X^1$, $X^2$, and A are as defined above in formula (I);

L^L is a neutral bidentate ligand coordinated to the central metal atom M through two atoms which may be the same or different, each of which is independently selected from the group consisting of a phosphorus atom, a nitrogen atom and an arsenic atom; and $L^{14}$ is selected from the group consisting of a $C_1$–$C_{20}$ alkyl, a $C_3$–$C_{20}$ carbene neutral electron donor ligand, a solvent molecule capable of coordinating with the central metal M, and a halide; and n is 1 when $L^{14}$ is a halide, and n is 2 when $L^{14}$ is an alkyl, a carbene ligand, or a solvent molecule.

The neutral electron donor ligand in the complexes of the invention is any ligand which, when removed from the central metal atom in its closed shell electron configuration, has a neutral charge, i.e., is a Lewis base. Preferably, the neutral electron donor ligand is a sterically encumbered ligand. Examples of such sterically encumbered neutral electron donor ligands are phosphine, sulfonated phosphine, phosphite, phosphinite, phosphonite, arsine, stibine, ether, amine, amide, imine, sulfoxide, carboxyl, nitrosyl, pyridine, and thioether.

In a preferred embodiment, $X^1$ is an allyl group and $X^2$ is a $C_3$–$C_{20}$ hydrocarbon group with an allyl moiety as an end group, the $C_3$–$C_{20}$ hydrocarbon group with an allyl moiety as an end group being optionally substituted on its backbone with up to three substituents independently selected from the group consisting of a $C_1$–$C_{20}$ alkyl, a $C_1$–$C_{20}$ alkoxy, and a $C_6$–$C_{12}$ aryl, and further optionally having up to three functional groups independently selected from the group consisting of hydroxyl, nitro, a halogen, thiol, thioether, ketone, aldehyde, ester, ether, amine, imine, amide, carboxylic acid, disulfide, carbonate, isocyanate, carbodiimide, carboalkoxy, and carbamate.

In another preferred embodiment, $X^1$ and $X^2$ taken together constitute a group resulting from the dimerization of isoprene units, said group resulting from the dimerization of isoprene optionally having on its backbone up to three substituents as described above, and further optionally having up to three functional groups as described above.

$L^1$ and $L^3$ in the catalysts of formula (I) may be the same or different, and may be any neutral electron donor ligand. In a preferred embodiment, each of $L^1$ and $L^3$ is independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether. In a more preferred embodiment, each of $L^1$ and $L^3$ is independently a phosphine of the formula $PR^1R^2R^3$, wherein $R^1$ is a $C_3$–$C_{12}$ secondary alkyl or a $C_5$–$C_{12}$ cycloalkyl, and each of $R^2$ and $R^3$, which may be the same or different, is independently selected from a $C_6$–$C_{12}$ aryl, a $C_1$–$C_{12}$ primary alkyl, a $C_3$–$C_{12}$ secondary alkyl or a $C_5$–$C_{12}$ cycloalkyl. In another preferred embodiment, $L^1$ and $L^3$, which may be the same or different, are independently selected from P(cyclohexyl)$_3$, P(cyclopentyl)$_3$, P(isopropyl)$_3$, and P(tertbutyl)$_3$.

In another embodiment of the catalysts represented by formula (I), each of $L^1$ and $L^3$, which may be the same or different, is independently selected from amines of the formula $NR^1R^2R^3$, wherein $R^1$ is a $C_3$–$C_{12}$ secondary alkyl, a $C_5$–$C_{12}$ cycloalkyl, and each of $R^2$ and $R^3$, which may be the same or different, is independently selected from the group consisting of a $C_6$–$C_{12}$ aryl, a $C_1$–$C_{12}$ primary alkyl, a $C_3$–$C_{12}$ secondary alkyl or a $C_5$–$C_{12}$ cycloalkyl.

In another preferred embodiment, each of $L^1$ and $L^3$ is independently selected from N(ethyl)$_3$ and N(methyl)$_3$.

The $L^2$ group in formula (I) is a carbene which may be derived from, for example, tert-butyl acetylene, phenyl acetylene or tri-methyl-silyl acetylene.

In the complexes represented by formula (II), $L^{11}$ may be any neutral donor ligand, $L^{12}$ is a solvent molecule capable of coordinating to the central metal M, $L^{13}$ is an alkyl substituent as described above, and the anion A is as described above and in more detail below. $L^{12}$ is any solvent that has the capability of occupying one coordination site of the metal atom, such as a solvent having an oxygen, nitrogen, sulfur or selenium atom which possesses the ability to coordinate to the metal. Preferred examples of such solvent are tetrahydrofuran (THF), acetonitrile, pyridine, triethyl amine, thiophene and thiol.

In the complexes represented by formula (I) or (III), the halide may be chloride, bromide, iodide or fluoride.

In the complexes represented by formula (III), L and L together constitute a bidentate ligand coordinated to the central metal M through phosphorus, nitrogen, or arsenic atoms or a combination thereof. The bidentate ligand L^L preferably has up to 30 carbon atoms and up to 10 heteroatoms selected from phosphorus, nitrogen and arsenic. Examples of the bidentate ligand L^L are 1,2-bis (diphenylphosphino)ethane, 1,2-bis(diphenylarsino)ethane, bis(diphenylphosphino)methane, ethylenediamine, propylenediamine, diethylenediamine, arphos (i.e., arsine phosphine), phen (i.e., phenanthroline), bpy (i.e., bipyridine), and αdi-imine.

In the catalysts represented by formulas (I), (II) or (III), the anion A that is very weakly coordinated to the central metal atom may be derived from any tetra coordinated boron compound, or any hexa coordinated phosphorus compound. The weakly coordinated anion may be also any one of the following: $BF_4$; $PF_6$; $ClO_4$; or fluorinated derivatives of $BPh_4$. The anion may be also derived from $Ph_3BCNBPh_3$ or a carba-closo-dodecaborate ($CB_{11}H_{12}$) and related compounds. The anion further may be derived from a pentafluorooxotellurate ($OTeF_5$), or any one of $HC(SO_2CF_3)_2$; $C_{60}$ (i.e., fullarene); $B(o-C_6H_4O_2)_2$; $H(1,8-BMe_2)_2C_{10}H_6$; or any of the anionic methyl aluminoxanes.

Some preferred examples of the catalysts of the invention are:

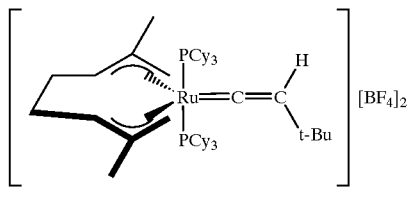

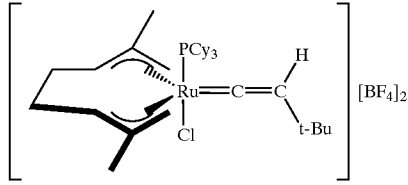

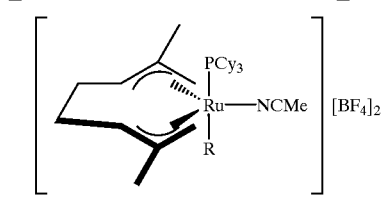

where R = Me or n-Bu

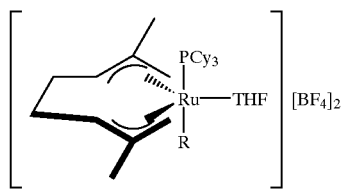

where R = Me or n-Bu

The catalysts of the invention are stable in the presence of a variety of functional groups including hydroxyl, thiol, ketone, aldehyde, ester, ether, amine, imine, amide, nitro, carboxylic acid, disulfide, carbonate, isocyanate, carbodiimide, carboalkoxy, and halogen. Hence, the starting materials and products of the reactions described below may contain any one or more of these functional groups without poisoning the catalyst. Furthermore, these catalysts are stable in aqueous, organic, or protic solvents, for example aromatic hydrocarbons, chlorinated hydrocarbons, ethers, aliphatic hydrocarbons, alcohols, water, or mixtures thereof. Therefore, the preparation of the catalysts may be carried out in one or more of these solvents without poisoning the catalyst product.

The present invention provides a simple synthetic procedure for a variety of ruthenium and osmium catalysts derived from the $[(allyl)MCl_2]_2$ dimer complex represented by formula I'. The process results in good product yield without the need for expensive and sophisticated equipment. Furthermore, the method can produce catalysts in a form which does not require post purification of the synthesized materials. The complexes are robust and resist degradation in the presence of air and/or moisture. Therefore polymerization experiments can easily be carried out in bottles using solvents that have been peripherally purged and degassed.

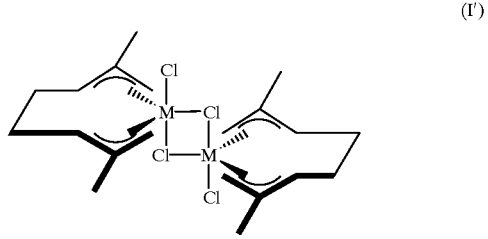

(I')

The syntheses are described below for a preferred catalyst wherein M is ruthenium, $L^1$ and $L^3$ are neutral donor electron ligands which are both tricyclohexyl phosphine ligands, or $L^1$ is tricyclohexyl phosphine and $L^3$ is a chloride; $L^2$ is also a neutral donor ligand which is a carbene; $X^1$ and $X^2$ together form the bidentate ligand 2,7-dimethyloctadienediyl; and A is the $BF_4$ anion. The formation of this catalyst can be accomplished by contacting a compound of formula I' with a solvent that has a capability for coordinating to the central metal atom. In this example, the solvent used is tetrahydrofuran. To the resultant product a compound of the formula $B^+A^-$ is added to precipitate out the chloride salt. In this example of the invention silver tetrafluoroborate ($AgBF_4$) is used as the salt to precipitate AgCl from the reaction. This step is critical because, depending on the stoichiometry of the compound added, various potential complexes can be made. The next step is the addition of the neutral donor ligand, i.e., the tricyclohexyl phosphine ligand. Addition of tert-butyl acetylene results in the formation of the active carbene complex.

In another aspect of the catalyst synthesis according to the present invention, a solvent wherein the donor atom is nitrogen, e.g., acetonitrile or pyridine, is brought in contact with the compound of formula I'. To the resulting solution a stoichiometric quantity of a compound of the formula $B^+A^-$ is added to precipitate out the chloride salt. In an embodiment of the invention ammonium hexafluorophosphate ($NH_4PF_6$) or thallium hexafluorophosphate ($TlPF_6$) is used as the salt to precipitate out $NH_4Cl$ or $TlCl$ from the reaction. The neutral donor ligand possessing sterically encumbering substituents, e.g., tricyclohexyl phosphine, is added to the solution. Following work up, addition of an alkyl lithium to the recovered product results in the formation of the active alkyl catalyst.

General Synthetic Schemes

The catalysts of the invention may be synthesized using readily available stable starting materials. The formation of complexes described in detail below can be completed generally in a couple of days, and the percent yield obtained in most cases is good to excellent. Specifically, the complexes can be synthesized readily by adding the appropriate reagents in stoichiometric quantities starting from the $[(allyl)MCl_2]_2$ dimer of formula I'.

The synthesis of the complexes of the invention does not require stringent methodologies typical of organometallic syntheses, and the formation of most of these complexes can be accomplished in approximately two days. The syntheses are generally carried out at room temperature with minimum constraints. The reactions are sufficiently clean with practically no side or competing reactions occurring simultaneously. Therefore, post purification of the isolated complexes is usually not required, and since the yield of these catalysts is typically greater than 90% it is quite commercially viable.

We have discovered two routes for synthesizing these complexes, both of which result in practically quantitative yields. The reaction schemes are illustrated below for the preparation of ruthenium catalysts, which are currently more commercially attractive because they are less expensive than the corresponding osmium compounds. The synthesis of the osmium catalysts according to the invention may be carried out by processes similar to those illustrated below for ruthenium catalysts.

In both routes of synthesis for the ruthenium catalysts, the starting material is the [(allyl)RuCl$_2$]$_2$ dimer complex, wherein the allyl in this example is the 2,7-dimethyloctadienediyl ligand.

tity of the neutral electron donor ligand (for example, tricyclohexyl phosphine) is added. This addition of the neutral donor ligand can be regulated in such a way that when two molar equivalents are added, one forms the halogen-substituted complex 1. On the other hand when four equivalents of the neutral donor ligand are added, the bis-phosphine-substituted complex 2 is formed. The reaction is allowed to continue for two hours at ambient temperature, preferably under a blanket of nitrogen or any inert gas. To this solution is added the tert-butylacetylene, or alternatively the trimethylsilyl acetylene, and the reaction is allowed to continue for 24 hours under ambient conditions. At the end of this period the carbene complex 3 or 4 is recovered from the reaction system.

In the alternate method, after dissolving the (allyl)RuCl$_2$ complex in the appropriate solvent and adding the silver tetrafluoroborate complex, the reaction is allowed to continue until complete precipitation of the silver halide has occurred. To this reaction mixture is added the appropriate neutral electron donating ligand and the reaction is allowed to continue further until the ligand-substituted complex is formed (this step can take anywhere between a few hours up

REACTION SCHEME A wherein Cy=cyclohexyl.

In the first route, Reaction Scheme A shown above, the [(allyl)RuCl$_2$]$_2$ dimer complex is dissolved in THF and a stoichiometric amount of AgBF$_4$ (or alternatively NH$_4$PF$_6$ or TlPF$_6$) in two or four equivalents, depending upon which complex is sought, is added to the stirred solution. After the precipitation of halide salt is completed, the solution is filtered through a short column of diatomaceous earth (2×2 cm), and to the eluate the appropriate stoichiometric quanto one day). Finally, the acetylene complex is added and the reaction allowed to continue for one day so that formation of the carbene complex takes place. In both methods described above the complexes can be recovered in very good yields.

For the formation of the alkyl-substituted ruthenium complexes, shown below in Reaction Scheme B, the initial procedure is almost the same as that described for the formation of the carbene complexes.

Reaction Scheme B

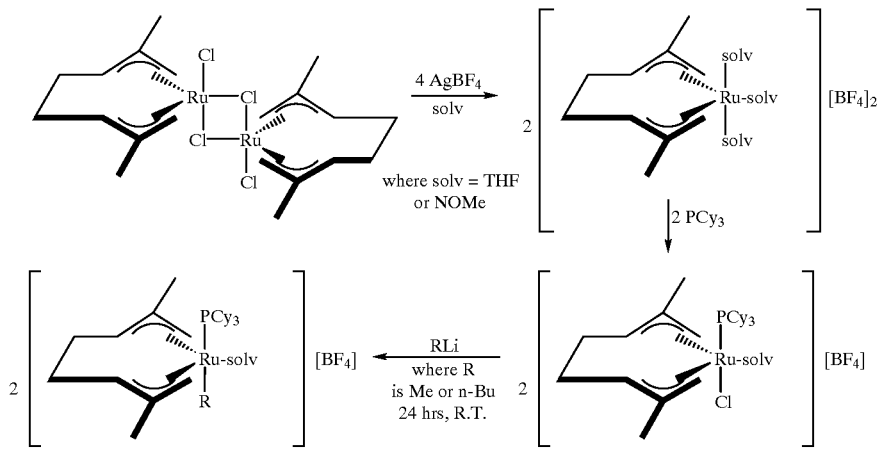

The alkyl complexes can also be prepared by following the two synthetic routes described above for the formation of the carbene complexes. In the first pathway, after the initial formation of the neutral electron donor ligand complexes, the reaction mixture is filtered and the appropriate alkyl lithium complex is added to procure the alkyl-substituted ruthenium complex. Alternatively, each of the compounds that make up the recipe for these complexes can be consecutively added to the reaction mixture (after the preceding, reaction has gone to completion) until the final step, at which point the appropriate alkyl lithium complex is added and following work up the desired complexes are recovered.

The complex catalysts of the invention are effective in initiating metathesis reactions in olefins. In particular, they are highly effective catalysts for the polymerization of olefins which may be cyclic olefins or acyclic olefins, the latter having at least two double bonds in a molecule. The cyclic olefins may be monocyclic, bicyclic or tricyclic, and include ring-strained cyclic olefins such as norbornene and derivatives thereof, dicyclopentadiene and derivatives thereof, and trans-cyclo octadiene and derivatives thereof, as well as unstrained cyclic olefins including those having at least five carbon atoms in the ring such as cyclopentene, cycloheptene, transcyclooctene, etc. These olefins, whether cyclic or acyclic, may optionally have one to three substituents. Examples of such substituents are alkyl or a functional moiety such as hydroxyl, nitro, a halogen, thiol, thioether, ketone, aldehyde, ester, ether, amine, imine, amide, carboxylic acid, disulfide, carbonate, isocyanate, carbodiimide, carboalkoxy, and carbamate.

In a preferred embodiment of the invention, the complexes of the invention can initiate the ring opening metathesis polymerization (ROMP) of ring strained cyclo-olefin monomers like NB or DCPD without the use of any co-catalyst (such as diazo ethyl acetate). The ROMP of NB is practically instantaneous, and monomer to catalyst ratios of 10,000:1 effortlessly produce quantitative conversions. Even at a very low ratio of catalyst such as 50,000:1 the conversion was extremely promising. For DCPD we have discovered that the experimental conditions must be controlled appropriately for obtaining higher conversions. For example, with a ruthenium carbene complex at ambient temperatures practically no conversion occurs. However, when the polymerization is carried out at elevated temperatures, i.e., 1 hour at 50° C. followed by 1 hour at 100° C., it was observed that the percent conversion is greater than 70% at monomer to catalyst ratios of 1000:1 or even 2000:1.

Most of the complexes of the invention can be used in the presence of air. However, when oxygen and moisture are excluded from the system the activity demonstrated by these catalysts increases.

The following examples further illustrate aspects of the invention but do not limit the invention. Unless otherwise indicated, all parts, percentages, ratios, etc., in the examples and the rest of the specification are on the basis of weight.

EXAMPLES

Synthesis of Catalysts
1) Formation of [(allyl)Ru(PCy$_3$)$_2$(=C=C(H)(tert-Bu)] [BF$_4$]$_2$ (catalyst a) or [(allyl)Ru(PCy$_3$)(=C=C(H)(tert-Bu) Cl][BF$_4$](catalyst b)

In two 50 mL Schlenk flasks equipped with a magnetic stirrer was placed approximately 500 mg (0.8 mmoles) of the [(allyl)RuCl$_2$]$_2$ dimer complex. The complex was dissolved in THF and after about 30 minutes 630 mg (3.2 mmoles), i.e., four molar equivalents of AgBF$_4$ were added to the first flask for the formation of complex (a) which is also the same as catalyst 3 shown in Scheme A above, and 315 mg (1.6 mmoles) were added to the second flask for the formation of complex (b) which is also the same as catalyst 4 shown in scheme A. The reaction was allowed to continue for about an hour by which time the entire amount of AgCl salt precipitated. The reaction mixtures were taken out of the glove-box and filtered through a short column of diatomaceous earth (2×2 cm) and returned to the flasks. Then, to the filtrate was added either 910 mg (3.2 mmoles), i.e,. four molar equivalents of the neutral donor ligand (PCy$_3$) for the formation of (a) or 455 mg (1.6 mmoles), i.e., two equivalents of PCy$_3$ for the formation of (b). These reactions were allowed to continue for approximately 6 hours at ambient temperatures, and at the end of this period the mixtures were once again filtered through a short column of diatomaceous earth to afford either the mono or the bis phosphine-substituted complexes. Finally, an excess amount of the tert-butylacetylene complex (~1 mL) was added to the mixture and the reaction was allowed to proceed at ambient temperature for approximately one day. At the end of this period, the reaction flask was attached to the vacuum manifold and the solvent was stripped under reduced pressure. The crude product obtained this way was pure for most purposes. However, the complexes can also be very easily recrystallized from dichloromethane.

2) One-pot Method

The synthesis of the complexes described above can also be readily accomplished by carrying out the procedure as a one-pot synthesis. In this method, the [(allyl)RuCl$_2$]$_2$ dimer complex was initially reacted with the AgBF$_4$ salt in THF solvent and after complete precipitation of the silver halide occurred, the neutral electron donor ligand (tricyclohexylphosphine) was added to the stirred solution. This reaction was then allowed to continue for several hours, and finally the tert-butylacetylene was added and the reaction was allowed to continue for another day. At the end of this period, the contents of the reaction were filtered and work up of the crude product was carried out as described above to afford the desired complex.

Characterization of the above carbene catalysts was carried out using $^1$H NMR spectroscopy:

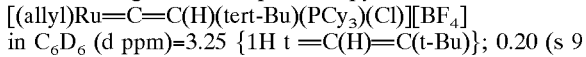

in C$_6$D$_6$ (d ppm)=3.25 {1H t =C(H)=C(t-Bu)}; 0.20 (s 9 H's t-butyl) 0.82–1.98 {36 H's CH$_2$'s from the cyclohexyl phosphine ligand}

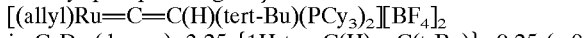

in C$_6$D$_6$ (d ppm)=3.25 {1H t =C(H)=C(t-Bu)}; 0.25 (s 9 H's t-butyl) 0.62–2.20 {72 H's CH$_2$'s from the cyclohexyl phosphine ligand}

3) Formation of [(allyl)Ru(N^N)(THF)][BF$_4$]$_2$ wherein (N^N) is Ar—N=C(H)—(H)C=N—Ar, wherein Ar is 2,6 di-isopropylaniline For the formation of this complex the [(allyl)RuCl$_2$]$_2$ dimer complex was charged into a 50 mL Schlenk equipped with a magnetic stirrer and dissolved in THF (~30 mL). Subsequently, AgBF$_4$ and the (N^N) di-imine ligand were added and after work up the crude product was retrieved and recrystallized using dichloromethane. The total yield obtained for this reaction was approximately 90%. A small portion of this complex was then converted to the carbene complex by addition of tert-butylacetylene.

4) Conversion to the carbene complex

The reaction of the di-imine substituted complex with tert-butylacetylene resulted in the formation of the carbene species by replacement of the THF by carbene. The procedure for the formation of this complex was the same as described for the other carbenes above.

5) Formation of alkyl ruthenium complexes:[(allyl)Ru(PCy$_3$)(S)(R)][BF$_4$] wherein S=solvent (THF or NCMe) and R=Me or n-Bu For the formation of these complexes, in two 50 mL Schlenk flasks equipped with a magnetic stirrer was placed approximately 500 mg (0.8 mmoles) of the [(allyl)RuCl$_2$]$_2$ dimer complex. This complex was dissolved in either THF or NCMe and after about 30 minutes 315 mg (1.6 mmoles), i.e., two molar equivalents of AgBF$_4$ were added to them. The reaction was allowed to continue for about an hour by which time the entire AgCl salt precipitated. The reaction mixtures were taken out of the glove-box and filtered through a short column of diatomaceous earth (2×2 cm) and returned to the flask. Next, to the filtrate was added 455 mg (1.6 mmoles), i.e., two equivalents of the neutral electron donor ligand (tricyclohexylphosphine) and the reactions were allowed to continue for approximately 6 hours at ambient temperatures. At the end of this period the contents were once again filtered through a short column of diatomaceous earth to afford the mono phosphine-substituted complexes. To this reaction mixture was next added an amount slightly more than a one molar equivalent of the respective alkyl lithium complex (either MeLi or n-BuLi) and after allowing the reaction to continue for one day, the desired products were isolated.

Polymerization of Cyclo-olefins

1) General description of polymerization of DCPD using ruthenium carbene complexes The formation of poly-DCPD can be quite conveniently achieved by reacting the ruthenium carbenes with endo-dicyclopentadiene (the monomer). In a typical reaction, approximately 2 mg of the desired ruthenium carbene complex is charged into a polymerization bottle, capped with a rubber septum and purged with argon before being taken inside a glove-box. To this is then added, approximately 0.5 mL to 1 mL of the monomer and the bottle is introduced into a constant temperature bath maintained at 50° C. The bottle is left in this bath for about 1 hour and then placed inside an oven at 100° C. for an additional hour. At the end of this period, the entire monomer component becomes very viscous portending the formation of the polymer. The polymer obtained in this manner is not completely soluble in common solvents, which is an indication that conducting the reaction at such elevated temperatures initiates some cross-linking reactions. However, we have discovered that when the molar ratio of the dicyclopentadiene to the ruthenium carbene complex is kept at or below 2000:1 and the polymerization is conducted in the above manner, the percent yield of the polymer obtained is nearly 75%.

2) General description of polymerization of NB using ruthenium complexes

Norbornene can be polymerized much more easily than dicyclopentadiene using any of the complexes described above. The reason for this enhanced reactivity of NB is because the catalyst has greater accessibility to coordinate to the double-bond (alkene moiety) of NB than DCPD and, therefore, formation of the metallo-cyclobutane ring in case of NB is much more facilitated. We have discovered that the ROMP of NB can occur practically quantitatively even when the molar ratios of the monomer to the catalyst are routinely kept above 10,000:1 and the reaction is carried out at ambient temperatures for less than one hour. The molecular weight of the polymer can be tailored effectively by the use of appropriate chain transfer agents, typically the use of long chained α-olefins like 1-hexene or 1-decene aid in the chain termination steps by acting as chain transfer agents and curtailing the molecular weights of the polymer.

3) General description of co-polymerization of NB with a vinyl-monomer using the ruthenium alkyl complexes The co-polymerization of NB with a vinyl-monomer like methyl acrylate (MA) can be carried out using the alkyl-substituted ruthenium complexes. In a representative experiment 0.5 gm each of NB and MA are mixed together in a polymerization bottle which is capped with a rubber septum and purged with argon. The bottle is taken inside a glove-box and to this is added approximately 2 mg of the [(allyl)Ru(PCy$_3$)(THF)(R)][BF$_4$] complex (wherein R is either Me or n-Bu) dissolved in 1 mL dichloromethane. The solution begins to become viscous immediately upon the addition of the catalyst. The bottle is next placed in a constant temperature bath maintained at 60° C. for one hour; at the end of this period the entire reaction mixture is practically solidified. The contents of the bottle are transferred to a Schlenk tube and attached to the vacuum line and subjected to evacuation overnight. The polymer obtained was weighed and found to be approximately 0.65 gm, which is an indication that some of the MA was also incorporated into the ROMP polymer. A $^1$H NMR of the polymer revealed a peak at 3.40 ppm diagnostic of the methyl group of the methyl acrylate. The AB 2:1:2:1 pattern of the $CH_2$ and the CH group of the poly-MA that occur between 1.6 and 2.0 ppm were hidden below the poly NB peaks. An FT-IR spectrum of the polymer revealed a carbonyl stretching frequency at 1645 $cm^{-1}$, which is an indication of the presence of a CO group within the polymer. The yield of the same polymerization when carried out with the NCMe solvent-coordinated molecule was lower than the one obtained with the THF coordinated complex.

Specific Examples of Polymerization

EXAMPLE 1

ROMP of DCPD using [(allyl)Ru(PCy)(=C=C(H)(tert-Bu)][$BF_4$]$_2$ and [(allyl)Ru(PCy$_3$)(=C=C(H)(tert-Bu)Cl][$BF_4$]

Polymerization of DCPD was carried out using both of the ruthenium carbene complexes described in the above synthesis examples. In a typical procedure 2 mg of the appropriate carbene complex was charged into polymerization bottles that were stoppered by means of a rubber septum and purged with argon. The bottles were taken inside the glove-box and into each one the appropriate quantity of the monomer (DCPD) was added (Table 1). After carrying out the polymerization according to the procedure described above the reactions were quenched using acetone and methanol. The polymers were recovered and dried on the vacuum line to determine the percent yield.

Initial Conditions of the Experiment

[Ru]=2 mg for each experiment. For the [(allyl)Ru{=C(H)C(t-Bu)(PCy$_3$)$_2$][$BF_4$]$_2$ complex DCPD=251 mg (1.89× $10^{-3}$ moles) for 1000:1; 502 mg (3.79×10moles) for 2000:1; 1.25 gm (9.45×$10^{-3}$ moles) for 5000:1; and 2.51 gm (18.90× $10^{-3}$ moles) for 10,000:1. For the (allyl)Ru{=C(H)C(t-Bu)(PCy$_3$)Cl][$BF_4$] complex DCPD=366 mg (2.77×$10^{-3}$ moles) for 1000:1; 732 mg (5.54×$10^{-3}$ moles) for 2000:1; 1.83 gm (13.85×$10^{-3}$ moles) for 5000:1; and 3.66 gm (27.70×$10^{-3}$ moles) for 10,000:1. No solvent was used in this study. Reaction was quenched using acetone and MeOH.

It should be noted that, although the polymer yield obtained with the chloride complex was less than with the bis phosphine complex, the yield of 20% obtained after 2 hours with the chloride complex at a catalyst:monomer ratio of 1:1000 to 1:5000 was nevertheless remarkable in view of the absence of a diazo cocatalyst.

EXAMPLE 2

Co-polymerization of NB and DCPD Using Ruthenium Complexes

Co-polymerization of NB and DCPD was carried out from the stand-point of trying to procure a more soluble polymer. Our previous experience had been that whenever the homo-polymerization of DCPD was carried out, the polymer obtained was partially soluble. Carrying out the polymerization in this manner incorporates the NB into the polymer chain and leads to a more pliable chain that has a greater tendency to go into solution. Thus all three carbene complexes described in detail herein were tested as catalysts. It was interesting to note that although the yields of the polymers were lower (about 50% as shown in Table 2) than those obtained previously for the homo-polymerization of DCPD, the yields were nevertheless acceptably high. Furthermore, the obtained polymers were far more soluble than those obtained earlier, which presents a process advantage.

TABLE 1

Homo-polymerization of DCPD using ruthenium carbene complexes:

| Expt # | Catalyst | Monomer | Ratio Cat:Monomer | Temp °C. | Time (hr) | Yield % |
|---|---|---|---|---|---|---|
| 1 | [(allyl)Ru{=C(H)C(t-Bu)(PCy$_3$)$_2$][$BF_4$]$_2$ | DCPD | 1:1000 | 50/100 | 1/1 | 78 |
| 2 | ↓ | ↓ | 1:2000 | ↓ | ↓ | 75 |
| 3 | ↓ | ↓ | 1:5000 | ↓ | ↓ | 30 |
| 4 | ↓ | ↓ | 1:10,000 | ↓ | ↓ | 11 |
| 5 | [(allyl)Ru{=C(H)C(t-Bu)(PCy$_3$)Cl][$BF_4$] | ↓ | 1:1000 | ↓ | ↓ | 20 |
| 6 | ↓ | ↓ | 1:2000 | ↓ | ↓ | 18 |
| 7 | ↓ | ↓ | 1:5000 | ↓ | ↓ | 25 |
| 8 | ↓ | ↓ | 1:10,000 | ↓ | ↓ | 10 |

TABLE 2

Co-polymerization of NB and DCPD using ruthenium carbene complexes:

| Expt # | Catalyst | Monomer | Ratio Cat:NB:DCPD | Time (hr) | Temp °C. | Yield % |
|---|---|---|---|---|---|---|
| 1 | [(allyl)Ru{=C=C(H)(t-Bu)(PCy$_3$)$_2$][$BF_4$]$_2$ | NB/DCPD | 1:100:2000 | 1/1 | 50/100 | ~50% |
| 2 | [(allyl)Ru{=C=C(H)(t-Bu)(PCy$_3$)Cl][$BF_4$] | ↓ | ↓ | ↓ | ↓ | ↓ |
| 3 | [(allyl)Ru{=C=C(H)(t-Bu)(N^N)][$BF_4$]$_2$ | ↓ | ↓ | ↓ | ↓ | ↓ |

Initial Conditions of the Experiment

[Ru]=2 mgs for each expt; NB and DCPD were added according to the ratios shown in the table No solvent was added, i.e., NB and DCPD were initially mixed and the catalyst was added to the mixture. The reaction was quenched with MeOH.

EXAMPLE 3

Co-polymerization of NB and MA Using Ruthenium Alkyl Complexes

Co-polymerization experiments for a cyclo-olefin monomer like NB and a vinyl monomer like MA were conducted to determine, if indeed, these two monomers could be incorporated into a single polymer. The alkyl ruthenium complexes (2 mg in each case) were dissolved in 1 mL $CH_2Cl_2$ and charged into polymerization bottles which were stoppered by rubber septa and purged with argon, and the bottles were then taken inside the glove-box. Next, the monomers (0.5 gm each) were separately weighed out and mixed in a beaker inside the glove-box. Thus, into each polymerization bottle a 1.0 gm aliquot of the monomers was added via a syringe. Both of the alkyl complexes (Me and n-Bu) with THF as the coordinated molecule appeared to initiate the polymerization much more rapidly than the complexes with the NCMe coordinated molecule. The bottles were introduced into a constant temperature bath maintained at 60° C. and the reaction was allowed to proceed for one hour. At the end of this period, MeOH was added to each of the bottles to quench the reaction and the polymer that precipitated were collected on frits and dried on the vacuum line overnight. The polymer yields (of about 45–48%) obtained with the NCMe complexes were lower than the yields (of about 60–65%) obtained with the THF complexes, as shown in Table 3. However, even the yields obtained with the NCMe complexes were in the ranges considered to be acceptable.

TABLE 3

Co-polymerization of NB and MA using ruthenium alkyl complexes:

| Expt # | Catalyst | Monomer | Ratio Cat:NB:MA | Temp ° C. | Time (hr) | Total Yield (%) |
|---|---|---|---|---|---|---|
| 1 | [(allyl)Ru(PCy$_3$)(NCMe)(Me)][BF$_4$] | NB/MA | 1:2000:2000 | 60 | 1 | ~45 |
| 2 | [(allyl)Ru(PCy$_3$)(NCMe)(n-Bu)][BF$_4$] | ↓ | ↓ | ↓ | ↓ | ~48 |
| 3 | [(allyl)Ru(PCy$_3$)(THF)(Me)][BF$_4$] | ↓ | ↓ | ↓ | ↓ | ~60 |
| 4 | [(allyl)Ru(PCy$_3$)(THF)(n-Bu)][BF$_4$] | ↓ | ↓ | ↓ | ↓ | ~65 |

Initial Conditions of the Experiment

[Ru]=2 mg for each experiment; NB and MA were initially mixed in a beaker and then syringed into the polymerization bottle under argon. The catalyst was dissolved in dichloromethane (1 mL) and syringed in. The reaction was quenched after 1 hour by adding MeOH.

Other embodiments of the present invention will be apparent to those skilled in the art from consideration of the specification and practice of the invention disclosed herein. It is intended that the specification and examples be considered as illustrative only, with the true scope and spirit of the invention being indicated by the following claims.

What is claimed is:

1. A compound represented by formula I

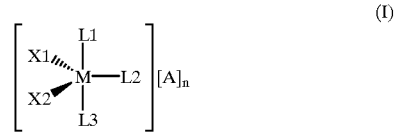

wherein M is ruthenium or osmium;

each of $X^1$ and $X^2$, which may be the same or different, is a $C_3$–$C_{20}$ hydrocarbon group having an allyl moiety as an end group bonded to the central metal atom M, optionally substituted on its backbone with up to three substituents independently selected from the group consisting of a $C_1$–$C_{20}$ alkyl, a $C_1$–$C_{20}$ alkoxy, and a $C_6$–$C_{12}$ aryl, and further optionally having up to three functional groups independently selected from the group consisting of hydroxyl, nitro, a halogen, thiol, thioether, ketone, aldehyde, ester, ether, amine, imine, amide, carboxylic acid, disulfide, carbonate, isocyanate, carbodiimide, carboalkoxy, and carbamate; or $X^1$ and $X^2$ together form a group which results from dimerization of a $C_4$–$C_{10}$ alkene and has at each end an allyl moiety bonded to the central metal atom M, said group resulting from the alkene dimerization being optionally substituted on its backbone with up to three substituents independently selected from the group consisting of a $C_1$–$C_{20}$ alkyl, a $C_1$–$C_{20}$ alkoxy, and a $C_6$–$C_{12}$ aryl, and further optionally having up to three functional groups independently selected from the group consisting of hydroxyl, nitro, a halogen, thiol, thioether, ketone, aldehyde, ester, ether, amine, imine, amide, carboxylic acid, disulfide, carbonate, isocyanate, carbodiimide, carboalkoxy, and carbamate;

$L^1$ is a neutral electron donor ligand;

$L^2$ is a carbene group represented by the formula

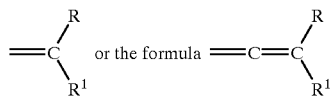

wherein each of R and $R^1$ is independently selected from the group consisting of hydrogen, $C_1$–$C_{20}$ alkyl, $C_2$–$C_{20}$ alkenyl, $C_2$–$C_{20}$ alkynyl, $C_6$–$C_{20}$ aryl, $C_1$–$C_{20}$ carboxylate, $C_1$–$C_{20}$ alkoxy, $C_2$–$C_{20}$ alkenyloxy, $C_2$–$C_{20}$ alkynyloxy, $C_6$–$C_{20}$ aryloxy, $C_2$–$C_{20}$ alkoxycarbonyl, $C_1$–$C_{20}$ alkylthio, $C_1$–$C_{20}$ alkylsulfonyl, and $C_1$–$C_{20}$ alkyl sulfinyl, wherein each of R and $R^1$ optionally may have up to three substituents selected from the group consisting of $C_1$–$C_5$ alkyl, a halogen, $C_1$–$C_5$ alkoxy, and $C_6$–$C_{10}$ aryl;

$L^3$ is a neutral electron donor ligand which may be the same as or different from $L^1$, or $L^3$ is a halide group;

A is a counter anion coordinated to the central metal atom M but only weakly coordinated so that A is not bonded as a ligand to the central metal atom M; and n is 1 when $L^3$ is a halide and n is 2 when $L^3$ is a neutral electron donor ligand.

2. A compound according to claim 1, wherein each of $L^1$ and $L^3$, which may be the same or different, is a neutral electron donor ligand.

3. A compound according to claim 2, wherein each of $L^1$ and $L^3$ is independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether.

4. A compound according to claim 2, wherein each of $L^1$ and $L^3$ is independently selected from the group consisting of phosphines of the formula $PR^1R^2R^3$, wherein $R^1$ is a $C_3$–$C_{12}$ secondary alkyl or a $C_5$–$C_{12}$ cycloalkyl, and each of $R^2$ and $R^3$, which may be the same or different, is independently selected from the group consisting of a $C_6$–$C_{12}$ aryl, a $C_1$–$C_{12}$ primary alkyl, a $C_3$–$C_{12}$ secondary alkyl and a $C_5$–$C_{12}$ cycloalkyl.

5. A compound according to claim 2, wherein each of $L^1$ and $L^3$ is independently selected from the group consisting of amines of the formula $NR^1R^2R^3$, wherein $R^1$ is a $C_3$–$C_{12}$ secondary alkyl, a $C_5$–$C_{12}$ cycloalkyl, and each of $R^2$ and $R^3$, which may be the same or different, is independently selected from the group consisting of a $C_6$–$C_{12}$ aryl, a $C_1$–$C_{12}$ primary alkyl, a $C_3$–$C_{12}$ secondary alkyl and a $C_5$–$C_{12}$ cycloalkyl.

6. A compound according to claim 1, wherein A comprises a tetra coordinated boron atom or a hexa coordinated phosphorus atom.

7. A compound according to claim 1, wherein A is selected from the group consisting of $BF_4^-$, $PF_6^-$, $ClO_4^-$, fluorinated derivatives of $BPh_4^-$, $Ph_3BCNBPh_3^-$, derivatives of carba-closo-dodecaborate $(CB_{11}H_{12})^-$, pentafluorooxotellurate $(OTeF_5)^-$, $HC(SO_2CF_3)_2^-$, $C_{60}^-$, $B(o$-$C_6H_4O_2)_2^-$, $H(1,8$-$BMe_2)_2C_{10}H_6^-$, and anionic methylaluminoxanes.

8. A compound according to claim 1, wherein $L^3$ is a halide.

9. A compound according to claim 1, wherein M is ruthenium.

10. A compound according to claim 1, wherein M is osmium.

11. A compound represented by any one of formula II or III

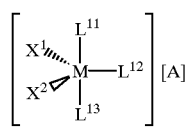

wherein M is ruthenium or osmium;

each of $X^1$ and $X^2$, which may be the same or different, is a $C_3$–$C_{20}$ hydrocarbon group having an allyl moiety as an end group bonded to the central metal atom M, said hydrocarbon group being optionally substituted on its backbone with up to three substituents independently selected from the group consisting of a $C_1$–$C_{20}$ alkyl, a $C_1$–$C_{20}$ alkoxy, and a $C_6$–$C_{12}$ aryl, and further optionally having up to three functional groups independently selected from the group consisting of hydroxyl, nitro, a halogen, thiol, thioether, ketone, aldehyde, ester, ether, amine, imine, amide, carboxylic acid, disulfide, carbonate, isocyanate, carbodiimide, carboalkoxy, and carbamate; or $X^1$ and $X^2$ together constitute a group which results from dimerization of a $C_4$–$C_{10}$ alkene and has at each end an allyl moiety bonded to the central metal atom M, said group resulting from the alkene dimerization being optionally substituted on its backbone with up to three substituents independently selected from the group consisting of a $C_1$–$C_{20}$ alkyl, a $C_6$–$C_{20}$ alkoxy, and a $C_6$–$C_{12}$ aryl, and further optionally having up to three functional groups independently selected from the group consisting of hydroxyl, nitro, a halogen, thiol, thioether, ketone, aldehyde, ester, ether, amine, imine, amide, carboxylic acid, disulfide, carbonate, isocyanate, carbodiimide, carboalkoxy, and carbamate;

$L^{11}$ is a neutral electron donor ligand;

$L^{12}$ is a solvent molecule capable of coordination to the central metal atom M;

$L^{13}$ is a $C_1$–$C_{20}$ alkyl;

A is a counter anion coordinated to the central metal atom M but only weakly coordinated so that A is not bonded as a ligand to the central metal atom M;

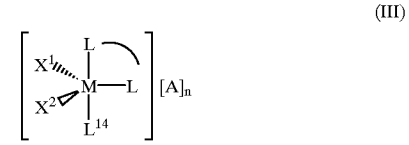

wherein M, $X^1$, $X^2$ and A are as defined above in formula (II);

L^L is a bidentate ligand coordinated to the central metal atom M through two atoms which may be the same or different, each of which is independently selected from the group consisting of a phosphorus atom, a nitrogen atom and an arsenic atom;

$L^{14}$ is selected from the group consisting of a $C_1$–$C_{20}$ alkyl, a $C_3$–$C_{20}$ carbene neutral electron donor ligand, a solvent molecule capable of coordination with the central metal M, and a halide; and n is 1 when $L^{14}$ is a halide, and n is 2 when $L^{14}$ is an alkyl, a carbene or a solvent molecule.

12. A compound according to formula II in claim 11, wherein $L^{11}$ is a neutral donor ligand containing phosphorus, nitrogen or arsenic.

13. A compound according to formula II in claim 11, wherein $L^2$ is a solvent molecule containing oxygen, nitrogen, sulfur or selenium.

14. A compound according to claim 13, wherein $L^2$ is selected from the group consisting of tetrahydrofuran, acetonitrile, pyridine, triethyl amine, thiophene and a thiol.

15. A compound according to claim 11, wherein A comprises a tetra coordinated boron atom or a hexa coordinated phosphorus atom.

16. A compound according to claim 11, wherein A is selected from the group consisting of $BF_4^-$, $PF_6^-$, $ClO_4^-$, fluorinated derivatives of $BPh_4^-$, $Ph_3BCNBPh_3^-$, derivatives of carba-closo-dodecaborate $(CB_{11}H_{12})^-$, pentafluorooxotellurate $(OTeF_5)^-$, $HC(SO_2CF_3)_2^-$, $C_{60}^-$, $B(o-C_6H_4O_2)_2^-$, $H(1,8-BMe_2)_2C_{10}H_6^{31-}$, and anionic methylaluminoxanes.

17. A compound according to claim 11, wherein M is ruthenium.

18. A compound according to claim 11, wherein M is osmium.

19. A compound according to claim 4, wherein each of $L^1$ and $L^3$ is independently selected from the group consisting of $P(cyclohexyl)_3$, $P(cyclopentyl)_3$, $P(isopropyl)_3$, and $P(tertbutyl)_3$.

20. A compound according to claim 5, wherein each of $L^1$ and $L^3$ is independently selected from the group consisting of $N(ethyl)_3$ and $N(methyl)_3$.

\* \* \* \* \*